United States Patent [19]

Gagnon

[11] Patent Number: 5,217,447
[45] Date of Patent: Jun. 8, 1993

[54] DIAPER SYSTEM WITH DETACHABLE LININGS

[75] Inventor: Normand A. Gagnon, Hamilton, Canada

[73] Assignees: Michael E. Fedryna; Peter H. T. Lee, Ontario, Canada

[21] Appl. No.: 552,932

[22] Filed: Jul. 16, 1990

[30] Foreign Application Priority Data

Jul. 17, 1989 [CA] Canada .................................. 605857

[51] Int. Cl.$^5$ ..................... A61F 13/15; A61F 13/20; A41B 9/00
[52] U.S. Cl. ................... 604/397; 604/358; 604/378; 604/385.1; 604/385.2; 604/391; 604/399; 2/400
[58] Field of Search ................. 604/391, 399, 385.1, 604/385.2, 397, 398, 396; 2/111, 112, 71, 73, 400-403, 406

[56] References Cited

U.S. PATENT DOCUMENTS

| 2,241,959 | 5/1941 | Potwin . | |
|---|---|---|---|
| 2,516,331 | 7/1950 | Miles | 604/398 |
| 2,532,029 | 11/1950 | Medoff . | |
| 2,545,761 | 3/1951 | Brink . | |
| 2,577,398 | 12/1951 | Blake . | |
| 2,731,014 | 1/1956 | Hollingsworth . | |
| 2,754,824 | 4/1956 | Blaufus . | |
| 2,793,642 | 5/1957 | Andruhovici . | |
| 2,826,199 | 3/1958 | Brandon . | |
| 2,967,526 | 1/1961 | Olson . | |
| 3,000,381 | 9/1961 | Mulhole et al. . | |
| 3,050,063 | 8/1962 | Margraf . | |
| 3,057,353 | 10/1962 | Casale . | |
| 3,162,196 | 12/1964 | Salk | 604/399 |
| 3,693,621 | 9/1972 | Jarusik et al. . | |
| 3,771,525 | 11/1973 | Chapuis | 604/372 |
| 3,842,838 | 10/1974 | Gellert | 604/378 |
| 3,900,032 | 8/1975 | Heurlen . | |
| 4,022,210 | 5/1977 | Glassman . | |
| 4,037,602 | 4/1977 | Hawthorne . | |
| 4,114,621 | 9/1978 | Mims, Jr. . | |
| 4,576,601 | 3/1986 | Brain . | |
| 4,578,073 | 3/1986 | Dysart et al. | 604/397 |
| 4,615,695 | 10/1986 | Cooper . | |
| 4,681,581 | 7/1987 | Coates . | |
| 4,798,603 | 1/1989 | Meyer et al. | 604/378 |
| 4,834,737 | 5/1989 | Khan | 604/385.2 |
| 4,842,594 | 6/1989 | Ness | 604/378 |
| 4,898,594 | 2/1990 | Cottenden | 604/397 |

FOREIGN PATENT DOCUMENTS

| 0558763 | 4/1960 | Belgium | 604/397 |
|---|---|---|---|
| 938401 | 12/1973 | Canada . | |
| 1207104 | 7/1986 | Canada . | |
| 82-8445 | 11/1982 | South Africa . | |

Primary Examiner—Randall L. Green
Assistant Examiner—Paul Zuttarelli
Attorney, Agent, or Firm—Wegner, Cantor, Mueller & Player

[57] ABSTRACT

A diaper assembly including a reusable over-garment having opposite side edges and two opposite ends and inner and outer surfaces and an absorbent liner adapted for positioning on the inner surface side of the over-garment. This liner also has opposite ends and inner and outer surfaces. There is a separate, disposable non-absorbent inner sheet adapted to cover the inner surface of the liner and having opposite ends. Preferably snap fasteners are provided for detachably connecting the opposite ends of both the liner and the inner sheet to respective opposite ends of the garment to enhance stability. Preferably a moisture proof sheet is disposed on the inner surface of the over-garment and this sheet has elasticized side edges.

29 Claims, 5 Drawing Sheets

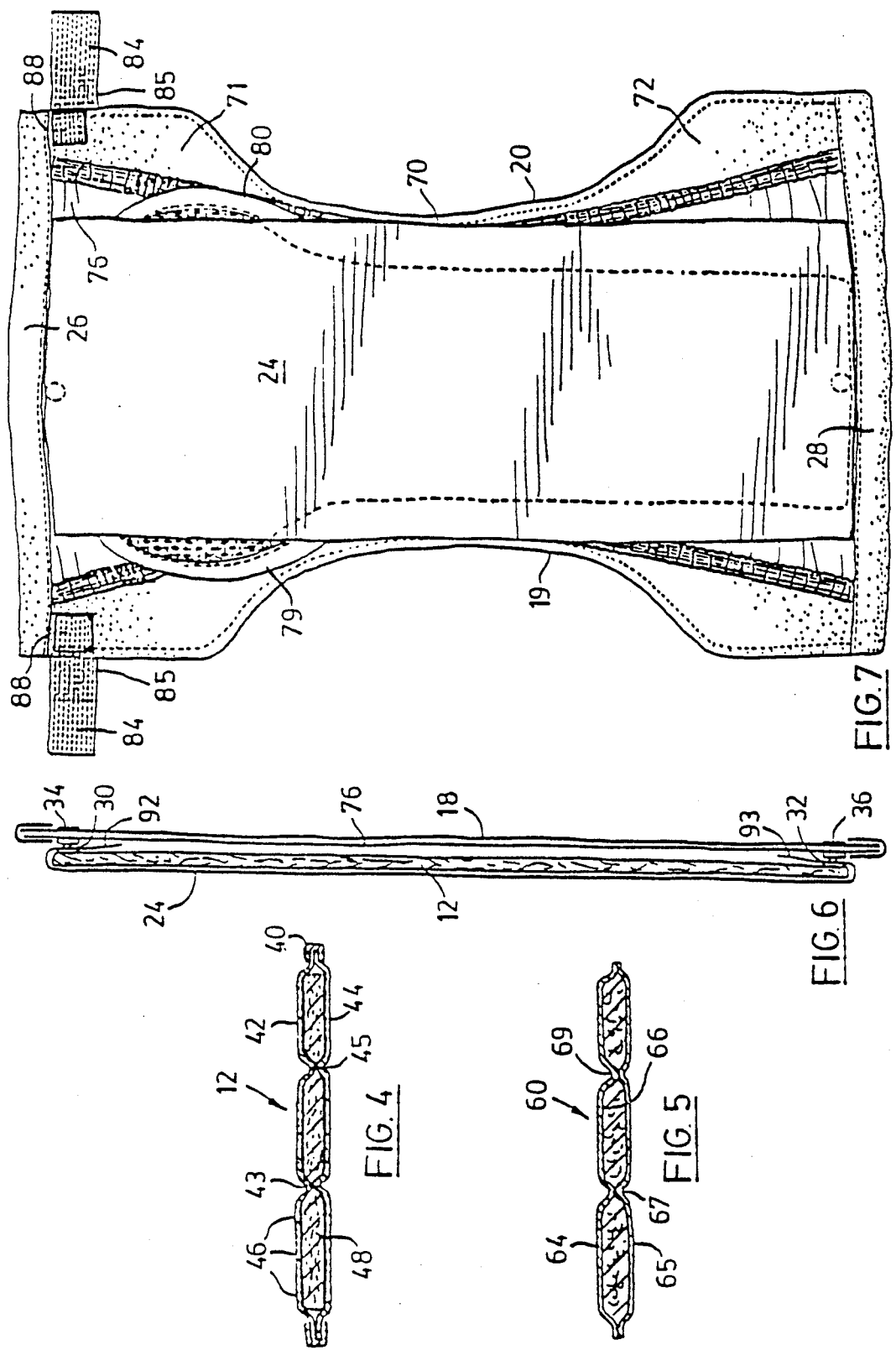

DIAPER SYSTEM WITH DETACHABLE LININGS

BACKGROUND OF THE INVENTION

This invention relates to a waste-containment garments both for infants and adults A variety of diaper constructions, both disposable and non-disposable are known in the art. In recent years there has been considerable emphasis on disposable diapers because of the convenience that they represent to the parents. However, disposable diapers are not entirely satisfactory for several reasons including the relatively high cost and the large amount of diaper material that must be disposed of after these diapers are used. It is estimated that over 16 billion disposable diapers are disposed of annually in the United States alone. Because most of these diapers use plastic materials that are disposed of with the diapers, they do not degrade quickly, thereby increasing the problem of disposal for municipalities and other operators of waste disposal sites. Also human excrement is often thrown out with the disposable diaper rather than being properly disposed of in a toilet. This creates a health hazard and can cause offensive odours.

Conventional cloth diapers which have been used for a considerable period of time are made by folding cloth in the appropriate manner and fastening the diaper by use of safety pins. The difficulty with safety pins is that they can possibly injure both the wearer and the person attaching the diaper by accidental puncture. With these conventional diapers an outer plastic pant often is required to prevent moisture penetration and leakage. The primary reason why these diapers have become less popular in recent years is the amount of laundering required to clean the diapers as they are used. Another problem in the maintenance of hygiene while using and cleaning these diapers.

Form-fitted elasticized cloth diapers have also been proposed in recent years. In some cases Velcro (trade mark) type fasteners are used to hold these diapers in place. Such diapers still require the use of an outer plastic pant.

Another known product employs a disposable top sheet for use with a cloth diaper. However there is no means for securing the top sheet in place and therefore the sheet is difficult to position and there is no assurance that it will remain in the appropriate position.

Recent U.S. Pat. No. 4,578,073 issued Mar. 25, 1986 to The Procter & Gamble Company describes a diaper construction wherein there is a disposable elasticized waste-containment insert that can be secured inside a non-elasticized outer garment such as a conventional re-usable diaper. The insert comprises an absorbent core and a liquid pervious, hydrophobic top sheet. The insert is so elasticized along its longitudinal side edges that, when properly secured inside the over-garment, the side edges form liquid seals or leg cuffs along upper thigh regions of the wearer.

Also U.S. Pat. No. 4,037,602 issued Jul. 26, 1977 to J. R. Hawthorne describes a diaper that can be adapted for use by either a boy or a girl. It is made from a substantially rectangular diaper sheet and a pair of trapezoidal liners mounted to the inside of this sheet. The bases of these liners are removably attached at the opposite ends of the diaper material and the tapered ends overlap at a central location. One of the liners can be removed and overlayed relative to the remaining liner so that the arrangement is particularly suitable for overnight use.

It is an object of the present invention to provide a diaper that combines the features of a cloth diaper with the convenience of a disposable diaper. It is a further object of the invention to provide a diaper that is easy to use but creates a minimum of disposable waste.

SUMMARY OF THE INVENTION

According to the present invention there is provided an improved diaper assembly wherein at least a major portion thereof is intended to be reusable, thus reducing substantially the amount of waste material that is generated with the use of such diapers. The diaper assembly disclosed herein is very convenient to use and is less costly than the use of common disposable diapers.

According to one aspect of the invention a diaper assembly comprises a reusable over-garment having opposite side edges and two opposite ends and inner and outer surfaces and a washable, reusable absorbent liner adapted for positioning on the inner surface of of the over-garment and having opposite ends and inner and outer surfaces as well. There is a separate, disposable, liquid pervious, non-absorbent, thin, flexible cover member adapted to cover the inner surface of the liner and having opposite ends. The cover member is completely detachable from the liner and over-garment to permit disposal of the cover member after use of the assembly. The length of the cover member exceeds the length of the liner. There are also means for detachably connecting the opposite ends of the liner and the cover member to respective opposite ends of the over-garment. The connecting means comprise snap fasteners attached at opposite ends of the over-garment and at opposite ends of the liner. End portions of the cover member can be folded back over the ends of the liner in order to be disposed between the liner and the over-garment and secured by the snap fasteners.

Because the preferred absorbent liner is washable and reusable, the amount of disposable waste material is reduced to a minimum.

According to another aspect of the invention a diaper assembly comprises a reusable over-garment having opposite side edges, two opposite ends and inner and outer surfaces, and a moisture proof sheet with elasticized side edges disposed on the inner surface of the over-garment and having two opposite side edges and two opposite ends, the latter ends being attached to the opposite ends of the over-garment while the opposite side edges are substantially free of attachment to the over-garment. The sheet has a stretched out length substantially equal to that of the over-garment. There is also a separate washable, reusable absorbent liner adapted for positioning over the moisture proof sheet and devices for detachably connecting the liner to the garment. The side edges of the moisture proof sheet are located a sufficient distance apart that the liner can be positioned at least substantially between the side edges. The side edges tend to pull the opposite ends of the over-garment towards one another.

According to a further aspect of the invention, a diaper assembly comprises a reusable over-garment having opposite side edges, two opposite ends, and inner and outer surfaces, and an absorbent liner made of washable cloth adapted for positioning on the inner surface of the over-garment and having opposite ends. This liner has a narrower section extending from one end thereof and through a central portion thereof and a wider section forming the other end thereof. A disposable, non-absorbent, liquid pervious, thin cover member covers the surface of the liner located furthest from the over-garment. There are also means for detachably connecting the cover member and the opposite ends of the liner to the opposite ends of the over-garment. The wider section of the liner can be placed selectively at either end of the over-garment.

According to still another aspect of the invention, a diaper assembly comprises a reusable washable over-garment having opposite side edges and two opposite ends and inner and outer surfaces; a washable, absorbent liner made of cloth material adapted for positioning on the inner surface of said over-garment and having opposite ends and inner and outer surfaces; a separate non-absorbent, disposable, liquid pervious, flexible cover member in the shape of a sleeve and sized to permit insertion of said absorbent liner therein so that said inner and outer surfaces of said liner are covered; and means for detachably connecting said opposite ends of said liner to respective opposite ends of said over-garment.

Further features and advantages of the present diaper assembly will be apparent from the following detailed description of preferred embodiments taken in conjunction with the accompanying drawings.

The invention is illustrated in particular and preferred embodiments by reference to the accompanying drawings.

BRIEF DESCRIPTION OF THE DRAWINGS

FIG. 4 is a cross-sectional view of the reusable liner of FIG. 2 taken along the line IV—IV;

FIG. 5 is a cross-sectional view of the absorbent, disposable liner, taken along the line V—V of FIG. 3;

FIG. 6 is a longitudinal edge view of an absorbent liner showing the manner in which the disposable non-absorbent sheet or cover member is placed thereon;

FIG. 7 is a plan view of a waste-containment garment constructed in accordance with the invention, which view shows the inside of the garment with the absorbent liner (shown in dashed lines) and a non-absorbent inner sheet or cover member placed therein;

DETAILED DESCRIPTION OF PREFERRED EMBODIMENTS

Figure 1:
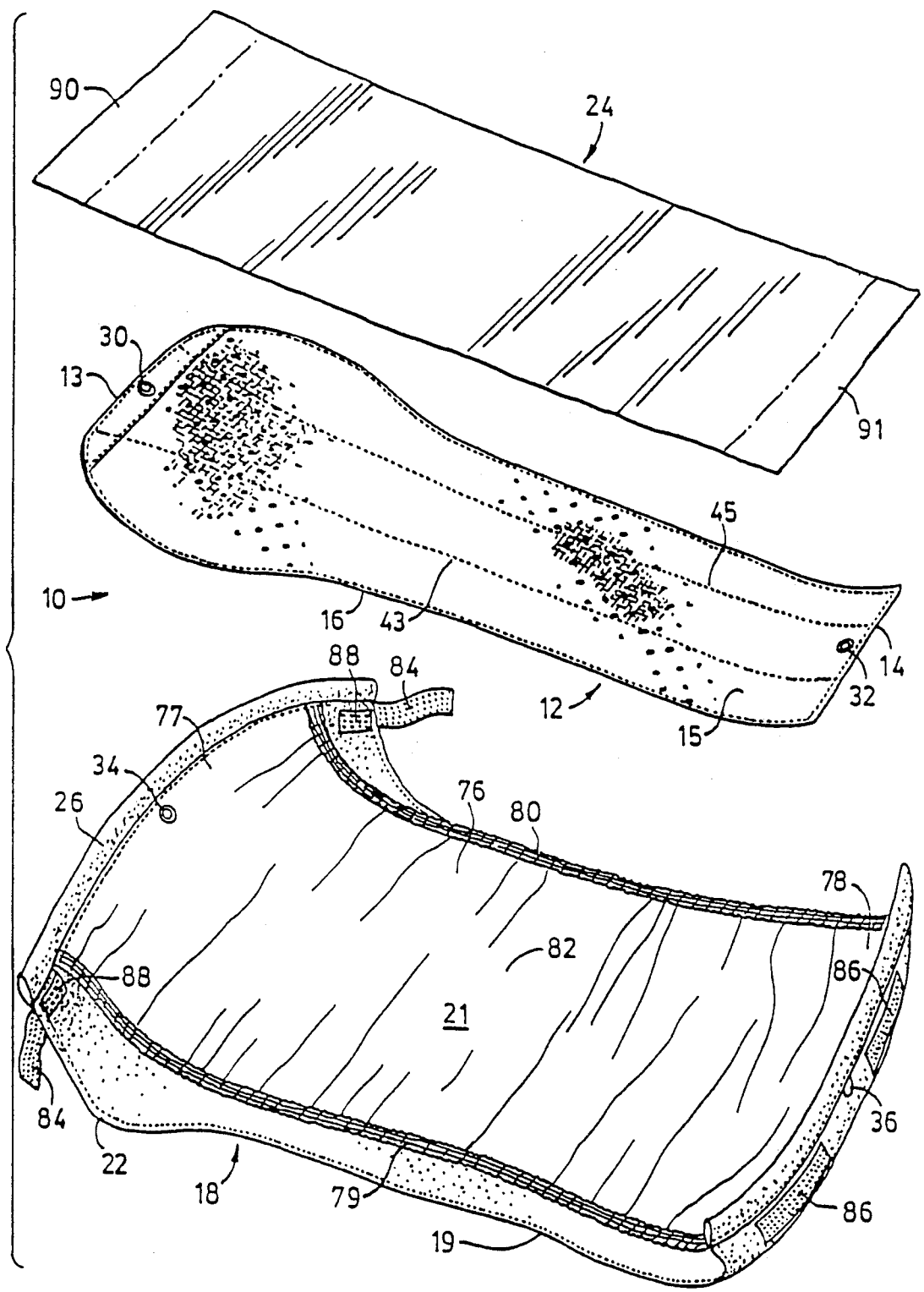
FIG. 1 is an exploded perspective view of an exemplary waste-containment garment constructed in accordance with the invention which comprises a reusable over-garment, an absorbent liner positioned on the inner surface of the garment, and a disposable, liquid pervious non-absorbent inner sheet adapted to cover the inner surface of the liner.

A preferred composite diaper assembly or waste-containment garment 10 is shown in FIG. 1. This diaper assembly includes an absorbent liner or insert 12 having opposite ends 13 and 14 and inner and outer surfaces 15 and 16, a reusable over-garment 18 having opposite side edges 19 and 20 and inner and outer surfaces 21 and 22, and preferably a separate, disposable, non-absorbent, liquid pervious inner sheet 24 which can have a rectangular shape. The inner sheet 24, which is thin and flexible, is also referred to herein as a cover member.

Figure 2:
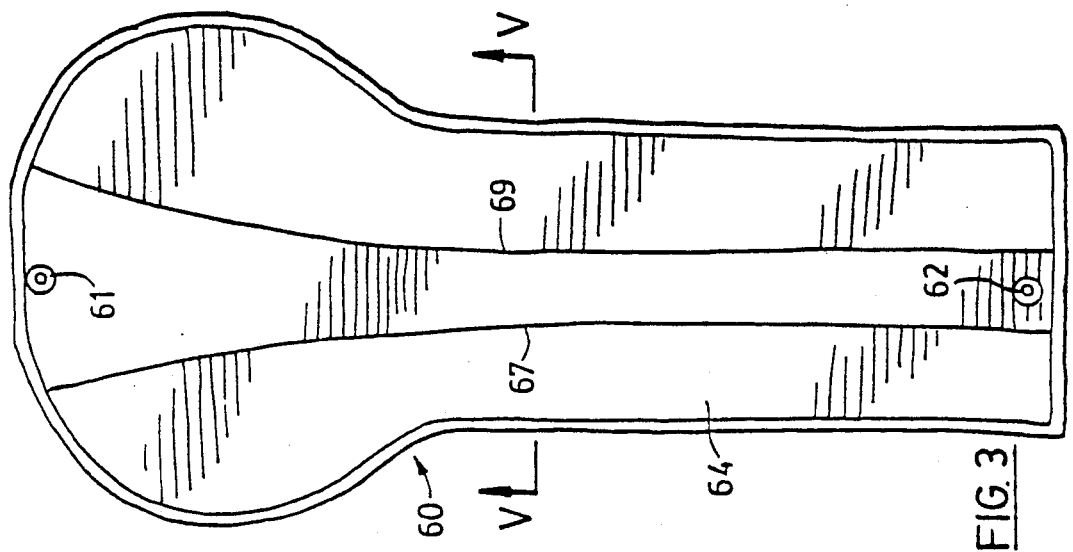
FIG. 2 is a plan view of an absorbent liner that is washable and is reusable.

The preferred construction of the absorbent liner 12 will now be described with particular reference to FIGS. 2 and 4 of the drawings. The preferred liner is both washable and reusable as is the aforementioned over-garment 18. There are means for detachably connecting the opposite ends 13 and 14 of the liner to respective opposite ends 26 and 28 of the over-garment. The preferred connecting means at each end is one half of a metal snap fastener indicated at 30 and 32. The fastener part 30 is adapted to connect to a co-operating fastener part 34 or fastener part 36, the latter being attached centrally at opposite ends of the over-garment. The liner 12 has a moisture repellant binding 40 extending about its perimeter and securing together the edges of top and bottom cloth layers 42 and 44. The preferred material for these top and bottom layers is a heavy knit-like hydrophobic jersey material having numerous holes 46 formed therein for the quick passage of fluid to a thick inner absorbent layer or pad 48. The inner pad has a high capacity for absorbing liquids, thereby reducing the likelihood of any leakage from the assembled diaper. Because the outer layers are highly porous, liquid will pass quickly into the absorbent inner pad and this will help to keep the user dry. A preferred material for the inner pad 48 is recycled cloth or an absorbent cloth-like material.

Preferably the outer layers of material 42 and 44 used on the liner 12 are selected to have low capillary action in order to assist in containment of fluids passing into the inner pad 48 and to prevent the liner from becoming unduly damp.

Preferably the outer layers are connected together by two continuous lines of stitching indicated at 43 and 45. This stitching adds stability to the liner, forms moisture banks to contain the spread of liquid, and increases the comfort of the garment for the wearer.

Figure 9:
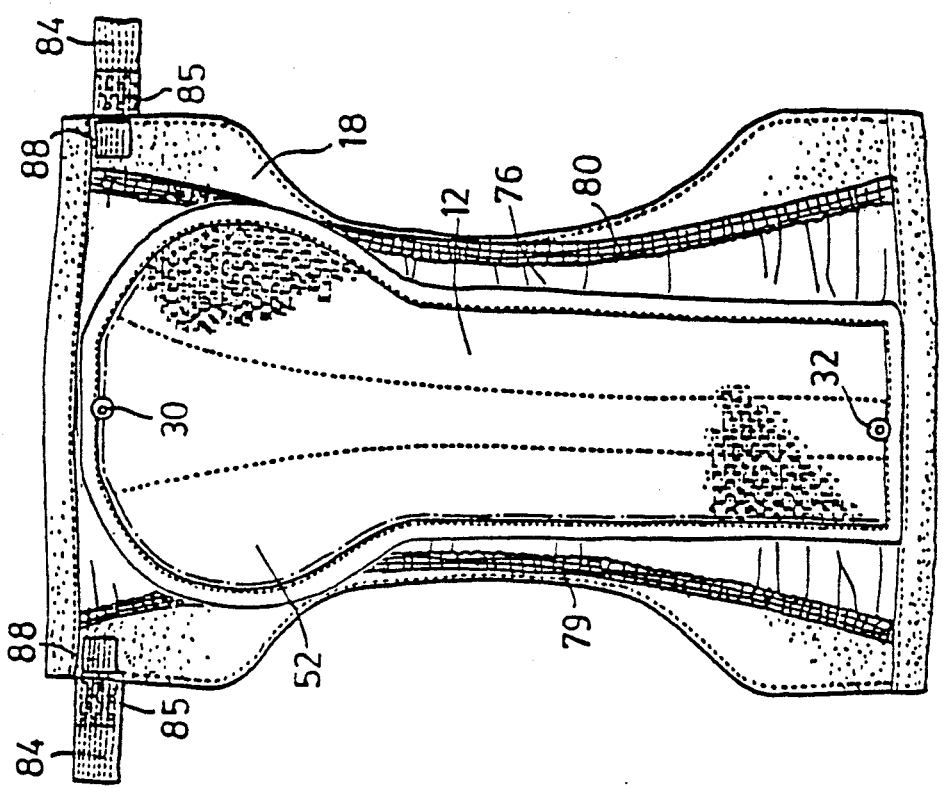
FIG. 9 is a plan view similar to FIG. 8 but showing the expanded end of the absorbent liner positioned at the rear of the garment.
Figure 8:
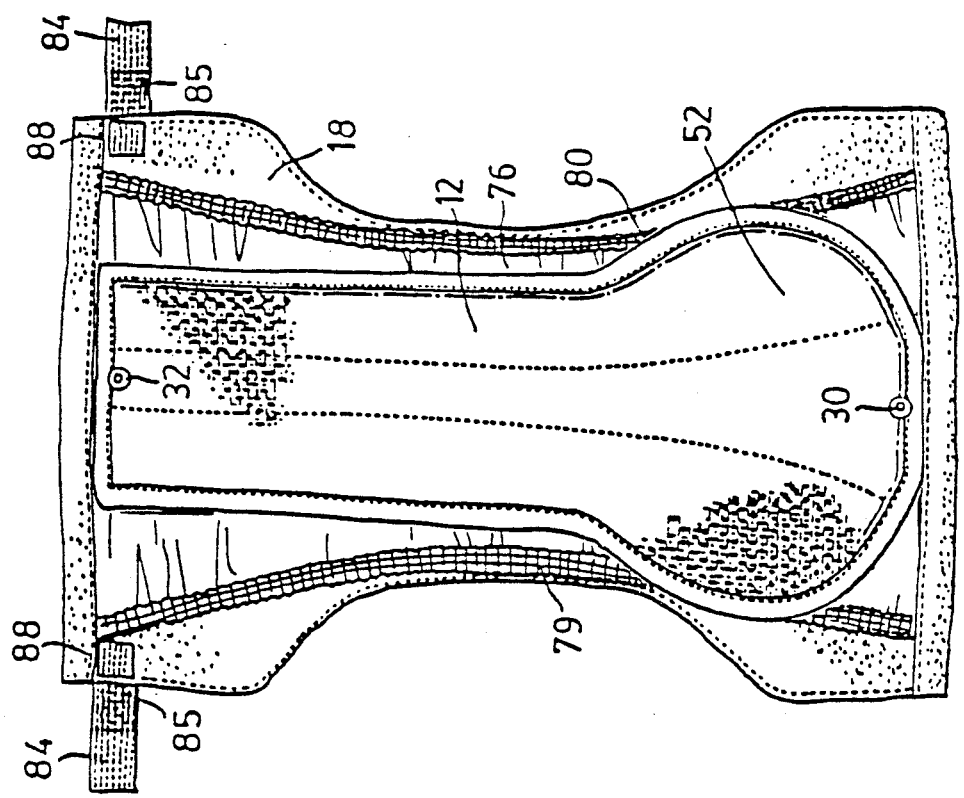
FIG. 8 is a plan view similar to FIG. 7 but showing the absorbent liner without an inner sheet covering same and showing the absorbent liner with an expanded end located at the front of the garment.

Because the absorbent liner 12 is detachably connected to the over-garment, it will be appreciated that different liners 12 can be used with the same over-garment or at different times of the day. For example, thinner lighter liners can be used during the day when less liquid absorbing capacity may be required while a thicker, more absorbent liner can be used at night time when maximum absorbency is required. Also, although a reusable liner of uniform width can be used in the present diaper assembly, the preferred shape of the liner is that shown in FIGS. 1 and 2. This preferred liner 12 has a narrower section 50 of uniform width extending from the end 14 thereof and through a central portion of the liner and a substantially wider section 52 forming an end portion thereof. This wider section which can be rounded as shown can selectively be placed either at the rear or the front of the assembly as illustrated in FIGS. 8 and 9 of the drawings. The orientation of the absorbent liner will depend upon whether the diaper is being used on a male or female person. The arrangement of FIG. 8 with the wider section 52 at the front of the diaper accommodates the normal urine flow for a male user. In this arrangement maximum capacity for absorbing fluid is located at the front of a diaper. The arrangement of FIG. 9 wherein the wider section 52 is at the rear of a diaper assembly accommodates the normal urine flow for a female. The positioning of the liner 12 may also depend upon the positioning of the infant in the crib or bed. For example if the infant normally lies on its stomach when sleeping the wider section 52 can be placed at the front of a diaper assembly. On the other hand if the infant or child is lying on its back, the wider section 52 can be placed at the rear of the diaper where maximum absorbency may be required.

Figure 3:
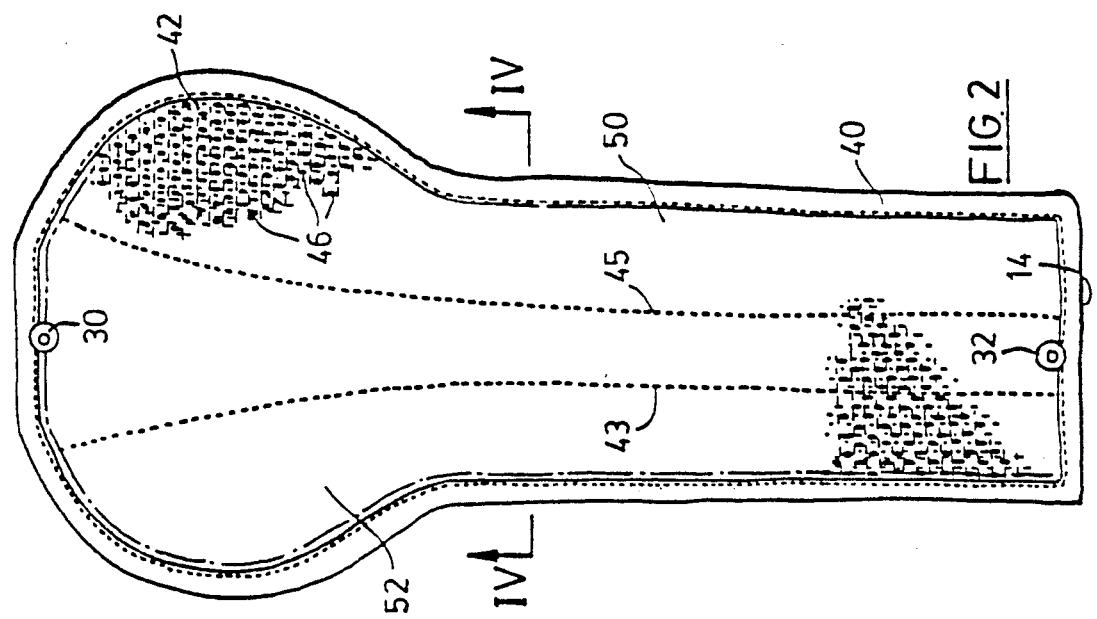
FIG. 3 is a plan view of an absorbent liner that is disposable after use.

With the present diaper assembly, it is also possible to have the absorbent liner constructed in such a manner that it is disposable after a single use. An absorbent liner 60 of this type is illustrated in FIGS. 3 and 5 of the drawings. This disposable liner preferably has the same shape in plan view as the reusable version shown in FIG. 2. Also it is equipped with the dome portion of a snap fastener at each end as indicated at 61 and 62. However these dome portions of the snap fasteners can be made of cheaper, plastic material, rather than metal, in order to reduce the cost of the disposable liner. The disposable liner can have outer layers made from a lightweight paper such as tissue paper having adequate structural integrity. These layers 64, 65 cover the front and back and are sealed together at the side edges of the liner as illustrated in FIG. 5. Between these outer layers is a highly absorbent thick layer of material which can be the same as that used for absorbency in standard disposable diapers. This absorbent layer is indicated at 66 in FIG. 5. Bleached wood pulp can be used for the absorbent inner material 66. As with the reusable liner the two outer layers are joined together along the lines indicated at 67 and 69 to form moisture banks. These connecting lines increase the structural integrity of the liner 60.

The preferred construction of the over-garment 18 will now be described with particular reference to FIGS. 1 and 7 of the drawings. The over-garment 18 can be a cotton weave material, patterned or decorated as desired. As shown it has straight edges at the front and rear ends 26 and 28. However the side edges 19 and 20 are preferable contoured in the manner illustrated clearly in FIG. 7 so as to form a narrower central section 70 and wider, rear and front sections 71 and 72. This contoured shape creates leg openings for the user and thus provides a more comfortable fit when the diaper is in place. Preferably the over-garment is hemmed along both sides and along both ends to improve its appearance and to provide a longer wear life for the garment.

In the preferred embodiment, a waterproof sheet 76 is disposed on the inner surface of the over-garment 18. This waterproof sheet has two opposite ends 77 and 78 attached to opposite ends of the over-garment. This waterproof sheet which can be generally rectangular has a width which is approximately equal to the width of the over-garment in its central section 70. It is attached at each end by folding over the cloth material of the over-garment so that the very end section of the plastic sheet is sandwiched between two cloth layers which are then sewn together to form the hem at the end of the over-garment. If desired the binding along the ends 26 and 28 can be elasticized by inserting and securing elastic strips or threads (not shown). As can be seen in FIG. 1, the eyelet portion of the snap fastener 34 extends through the the plastic sheet and the outer cloth. In this way the central recess of the 1 fastener is clear and open for attachment of the dome on the other part of the fastener, item 30 at the end of the absorbent liner.

Both longitudinal edges of the waterproof sheet 76 are elasticized as shown at 79 and 80. In this way the waterproof sheet fits snugly around the thighs of the infant or other user, helping to prevent any leakage or escape of any human excrement. The elasticized edges of the waterproof sheet also help to form the over-garment into a hammock-like shape as indicated in FIG. 1. Thus these elasticized edges tend to pull up or raise up the ends 26 and 28 of the over-garment. The elasticized edges 79 and 80 themselves tend to rise up above the central section 82 of the waterproof sheet and the over-garment. This desirable shape for the waterproof sheet/over-garment combination helps to locate and position both the absorbent liner 12 and the inner sheet 24.

Preferably the waterproof sheet 76 is made from treated plastic, vinyl or nylon material which is not only waterproof but resists cracking and tearing.

Velcro type hook fasteners 84 are attached at two corners of the over-garment for securing same in place on the wearer. Preferably these hook fasteners are attached to the outer surface of the over-garment and at the rear end thereof. The hook side of each fastener faces upwardly and inwardly when the over-garment is arranged in the manner shown in FIG. 1. If desired each hook fastener 84 can be provided with an elasticized piece or section at 85 to provide increased adjustment capability and improved comfort. Located at the front end of the over-garment are two further Velcro type fasteners 86 of the loop variety. These Velcro strips are arranged on opposite sides of the central snap fastener 36 and they are located on the outer surface of the over-garment near the end 28. It will be readily seen that the hook fasteners 84 can be engaged with the loop fasteners 86 when the over-garment has been put in place on the infant or other user. Also in order to assist in the washing of the over-garment, two additional loop fasteners 88 can be secured to the inner surface of the diaper close to the hook fastener 84. Thus when the over-garment is to be washed, it is easy to engage each hook fastener 84 with its respective loop fastener 88 in order that the hooks of the fastener strips 84 will not be exposed during washing. This will help to prevent the hook type fasteners 84 from being attached to other clothes while the over-garment is being washed or dried.

A preferred feature of the present diaper assembly is the provision of a disposable, non-absorbent, liquid pervious inner sheet or cover member 24 having opposite ends 90 and 91. The length of this inner sheet 24 exceeds the length of the absorbent liner 12. In this way end portions 92 and 93 of the inner sheet 24 can be folded back (as shown in FIG. 6) over the ends of the liner 12 in order to be disposed between the liner and the over-garment during use of the diaper. Because the inner sheet is quite thin and made of a very light material, the domes of the snap fasteners 30 and 32 can still be pushed into and secured in the sockets of fasteners parts 34 and 36 on the over-garment. In this way not only do the snap fasteners secure the absorbent liner 12 in place but they also secure opposite ends of the inner sheet 24 in place.

Preferably the inner sheet 24 is made from a hydrophobic non-woven material which can be polypropylene. Inner sheet 24 can be made of the same non-woven material as the inner layer of commonly used disposable diapers. In addition to help keeping the skin of the infant or other user dry, the disposable inner sheet has a distinct additional advantage that arises from the fact that it can be removed from the rest of the diaper and disposed of. Quite often the inner sheet will become soiled in use and will need to be replaced while the rest of the diaper assembly is still clean and dry. In such cases it is not necessary to wash or dispose of the remainder of the diaper assembly, there being only the need to replace the inner sheet. A further advantage provided by the preferred form of inner sheet is that it can easily be flushed down a toilet whereupon it will quickly disintegrate and disappear in the sewage system. If the inner sheet is disposed of in this manner, it should be made of a material that is readily biodegradable.

A further distinct advantage of the described inner sheet 24 arises from the fact that it is disposable and it is a sheet which is in immediate contact with the human excrement deposited in the diaper. The sheet permits human excrement to be easily disposed of down a toilet because it can be dropped into the toilet with the excrement. It will be appreciated that this arrangement tends to leave the absorbent liner 12 cleaner so that it is left in a more desirable condition for laundering.

Figure 10:
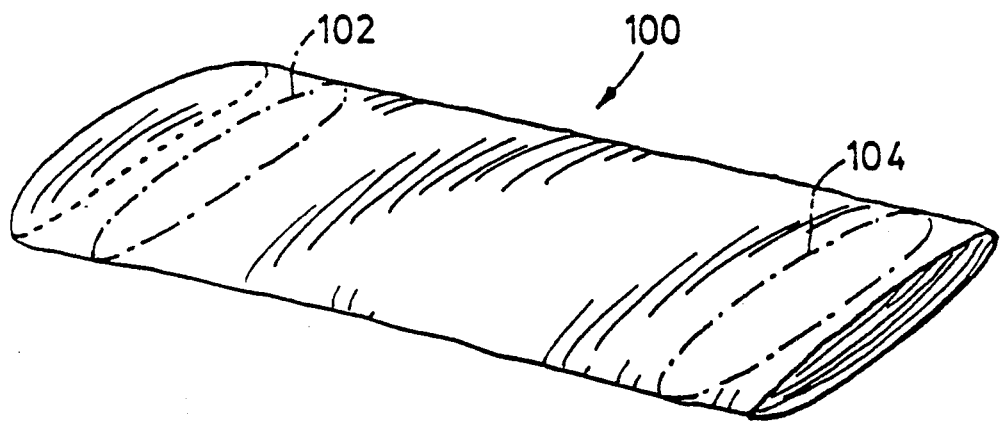
FIG. 10 is a perspective view of an alternate form of cover member in the shape of a sleeve.
Figure 11:
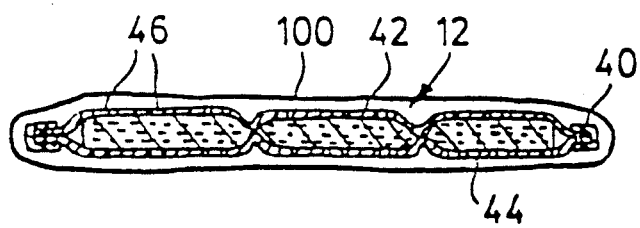
FIG. 11 is a cross-sectional view similar to FIG. 4 but showing the placement of the cover member of FIG. 10 around the reusable liner.

An alternate form of cover member identified by reference 100 in FIGS. 10 and 11 has the shape of a sleeve. The absorbent liner 12 fits completely into this preferred cover member when the diaper is assembled for use. Using the cover member 100 both inner and outer surfaces of the liner 12 are covered. As with the first version 24, the length of the cover member 100 exceeds the length of the liner. In this way end portions 102 and 104 can be folded back over the ends of the liner in order to be disposed between the liner and the over-garment. Thus the cover member 100 is secured in place by the use of the dome fasteners in substantially the same manner as the first version 24. The configuration of the cover member 100 also helps substantially in maintaining the proper position of the cover member. It is prevented from bunching up in the centre of the 1 diaper and exposing the absorbent liner.

It will be appreciated by those skilled in the diaper art that instead of using the described waterproof sheet attached to the inside of the over-garment, it would be possible to dispense with the use of such a sheet and to replace it with plastic outer pants of known construction. However a disadvantage of using these known outer pants is that the over-garment 18 will become soiled more easily because of fluids leaking through the absorbent liner and therefore the over-garment will have to be washed or cleaned more often. In the preferred construction using a waterproof sheet on the inside of the over-garment, it is generally possible to use the over-garment a number of times without the need for laundering.

Preferably the absorbent reusable liner 12 is sized so that it fits readily within the bounds of the waterproof sheet 76. Also instead of using bleached wood pulp as the thick absorbent layer in the disposable liner 60, one can use recycled cloth or a cloth-like material having high absorbency.

It will be appreciated that a diaper assembly constructed in accordance with the invention can be made for either infant or geriatric users. About four separate sizes for each of these two classes of users can be made. In the case of the much larger geriatric waste-containment garment, the primary difference over the infant diaper would be the 1 provision of additional Velcro type fasteners on opposite sides of the diaper so as to improve the fit and appearance of the larger garment.

It will be clear to those skilled in the construction and use of diapers that various modifications and changes can be made to the diaper assembly described herein. All such modifications and changes as fall within the scope of the appended claims are intended to be part of this invention.

I therefore claim:

1. A diaper assembly comprising:

a reusable over-garment having opposite side edges and two opposite ends and inner and outer surfaces, an elongate, washable, reusable absorbent liner adapted for positioning on the inner surface of said over-garment and having a length with opposite ends and inner and outer surfaces, an elongate, separate, disposable, non-absorbent, liquid pervious, thin, flexible cover member adapted to cover said inner surface of said liner and having a length with opposite ends, the length of said cover member exceeding the length of said liner and said cover member being completely detachable from said liner and over-garment to permit disposal of said cover member after use of said assembly, and means for detachably connecting said opposite ends of said liner and said cover member to respective opposite ends of said over-garment, said connecting means comprising snap fasteners attached at opposite ends of said over-garment and at opposite ends of said liner, wherein end portions of said cover member are foldable back over the ends of said liner in order to be disposed between said liner and said over-garment.

2. A diaper assembly according to claim 1 including a waterproof sheet with elasticized side edges disposed on the inner surface of said over-garment, having a length substantially equal to that of the over-garment and having two opposite ends permanently attached to said opposite ends of said over-garment, said elasticized side edges tending to pull said opposite ends of said over-garment towards one another.

3. A diaper assembly according to claim 1 wherein said cover member is made of non-woven, hydrophobic polypropylene.

4. A diaper assembly according to claim 1 wherein said opposite ends of said over-garment each have transverse center and said snap fasteners comprise two, metal snap fastener sets attached in said centers of said opposite ends of said over-garment and opposite ends of said liner.

5. A diaper assembly according to claim 1 including reusable hook and loop type fasteners attached to said opposite ends of said over-garment for securing said over-garment in place on a wearer.

6. A diaper assembly according to claim 1 wherein said cover member is in the form of a sleeve and said liner fits into said cover member when the diaper assembly is ready for use.

7. A diaper assembly according to claim 1 wherein said absorbent liner comprises top and bottom layers of reusable, hydrophobic cloth material separated by a highly absorbent inner layer of cloth material.

8. A diaper assembly according to claim 7 wherein said top layer of cloth material has numerous holes formed therein for quick passage of fluid therethrough.

9. A diaper assembly comprising:
a reusable over-garment having opposite side edges, two opposite ends, and inner and outer surfaces;
a moisture proof sheet with elasticized side edges disposed on the inner surface of said over-garment, having a length substantially equal to that of said over-garment, and having two opposite side edges and two opposite ends, The latter ends being permanently attached to said opposite ends of said over-garment while the opposite side edges are substantially free of attachment to said over-garment;
a separate washable, reusable absorbent liner adapted for positioning over said moisture proof sheet; and
means for detachably connecting said liner to said over-garment,
wherein said side edges of said moisture proof sheet are located a sufficient distance apart that said liner can be positioned at least substantially between said side edges of said moisture proof sheet, said side edges of said moisture proof sheet tending to pull said opposite ends of said over-garment towards one another.

10. A diaper assembly according to claim 9 wherein said absorbent liner has opposite ends joined by said connecting means to respective opposite ends of said over-garment.

11. A diaper assembly according to claim 9 wherein said connecting means comprise snap fasteners attached at opposite ends of said over-garment and said liner.

12. A diaper assembly according to claim 9 including reusable hook and loop type fasteners attached to said opposite ends of said over-garment for securing said over-garment in place on a wearer.

13. A diaper assembly according to claim 9 wherein said diaper assembly has a rear portion and a front portion for placement at a rear and a front of a user respectively, said liner has a narrower section of uniform width extending from one end thereof and through a central portion of the liner and a substantially wider section forming an end portion thereof and said wider section can be placed selectively either at the rear portion or the front portion of the assembly.

14. A diaper assembly according to claim 9 wherein said absorbent liner comprises top and bottom layers of reusable hydrophobic cloth material separated by a highly absorbent inner layer of cloth material.

15. A diaper assembly according to claim 14 wherein said top layer of cloth material has numerous holes formed therein for quick passage of fluid therethrough.

16. A diaper assembly comprising:
a reusable over-garment having opposite side edges, two opposite ends and inner and outer surfaces;
a moisture proof sheet with elasticized sheet edges disposed on the inner surface of said over-garment, having a length substantially equal to that of said over-garment, and having two opposite side edges and two opposite ends, the latter ends being permanently attached to said opposite ends of said over-garment while the opposite side edges are substantially free of attachment to said over-garment;
an absorbent liner made of washable cloth and adapted for positioning over said moisture proof sheet, said liner having opposite ends and non-overlapping narrower and wider sections, said narrower section extending from one end thereof and through a central portion thereof and terminating at said wider section which forms the other end thereof;
a disposable, non-absorbent, liquid pervious, thin cover member covering the surface of said liner located furthest from said over-garment; and
means for detachably connecting said cover member and said opposite ends of said liner to said opposite ends of said over-garment, said connecting means being reusable a number of times and washable with said liner,
wherein said wider section of said liner can be placed selectively at either end of said over-garment and secured to said over-garment by said connecting means; and
wherein said side edges of said moisture proof sheet are located a sufficient distance apart that said liner can be positioned at least substantially between said side edges of said moisture proof sheet, said side edges of said moisture proof sheet tending to pull said opposite ends of said over-garment towards one another.

17. A diaper assembly according to claim 16 wherein said cover member is made of nonwoven polypropylene.

18. A diaper assembly according to claim 16 wherein said absorbent liner comprises a relatively thick pad of high absorbency cloth covered by a reusable layer of cloth material having a large number of openings distributed over its surface.

19. A diaper assembly according to claim 16 wherein said connecting means comprise metal snap fasteners attached at opposite ends of said over-garment and said liner.

20. A diaper assembly according to claim 16 wherein said over-garment is made of cloth and is contoured along its side edges to provide leg openings.

21. A diaper assembly according to claim 16 wherein said thin cover member has a sleeve shape and said liner is inserted into said cover member.

22. A diaper assembly according to claim 21 wherein said cover member is made of nonwoven polypropylene.

23. A diaper assembly according to claim 16 wherein said absorbent liner comprises top and bottom layers of reusable, hydrophobic cloth material separated by a highly absorbent inner layer of cloth material.

24. A diaper assembly according to claim 23 wherein said top layer of clot material has numerous holes formed therein for quick passage of fluid therethrough.

25. A diaper assembly comprising:
a reusable, washable over-garment having opposite side edges, two opposite ends and inner and outer surfaces,
an elongate, washable, absorbent liner made of cloth material adapted for positioning on the inner surface of said over-garment and having a length with opposite ends and inner and outer surfaces,
an elongate, separate, disposable, non-absorbent, liquid pervious, flexible cover member having a sleeve shape with a length and sized to permit insertion of said absorbent liner therein so that said inner and outer surfaces of said liner are covered, the length of said cover member exceeding the length of said liner,
means for detachably connecting said opposite ends of said liner and said cover member to respective opposite ends of said over-garment, said connecting means being reusable a number of times and washable with said liner, wherein end portions of said cover member are foldable back over the ends of said liner in order to be disposed between said liner and said over-garment.

26. A diaper assembly according to claim 25 wherein said over-garment is made of cloth and is contoured along its side edges to provide leg openings and a moisture proof sheet is disposed on the inner surface of said over-garment and permanently attached thereto at opposite ends of said sheet.

27. A diaper assembly according to claim 25 wherein said cover member is made of polypropylene.

28. A diaper assembly according to claim 25 wherein said absorbent liner comprises top and bottom layers of reusable, hydrophobic cloth material separated by a highly absorbent inner layer of cloth material.

29. A diaper assembly according to claim 28 wherein at least said top layer of cloth material has numerous holes formed therein for quick passage of fluid therethrough.

* * * * *